United States Patent [19]
Dietz et al.

[11] Patent Number: 5,207,680
[45] Date of Patent: May 4, 1993

[54] FRONT MILLING GUIDE FOR USE IN ORTHOPAEDIC SURGERY

[75] Inventors: Terry L. Dietz, Columbia City; Richard D. Vanlaningham, Leesburg, both of Ind.

[73] Assignee: Zimmer, Inc., Warsaw, Ind.

[21] Appl. No.: 881,285

[22] Filed: May 11, 1992

[51] Int. Cl.⁵ .................... A61F 5/00; A61F 2/32
[52] U.S. Cl. .................................. 606/86; 606/96
[58] Field of Search ............. 606/96, 97, 98, 79, 606/80, 86, 87, 88

[56] References Cited

U.S. PATENT DOCUMENTS

| | | | |
|---|---|---|---|
| 1,985,108 | 12/1934 | Rush | 606/86 |
| 4,179,810 | 12/1979 | Kirsch | 606/87 |
| 4,467,801 | 8/1984 | Whiteside | 182/303 R |
| 4,474,177 | 10/1984 | Whiteside | 128/303 R |
| 4,567,886 | 2/1986 | Peterson | 606/88 |
| 4,664,102 | 5/1987 | Comparetto | 606/79 |
| 4,721,104 | 1/1988 | Kaufman et al. | 128/92 VW |
| 4,722,331 | 2/1988 | Fox | 606/80 |
| 4,757,810 | 7/1988 | Reese | 606/87 |
| 4,893,619 | 1/1990 | Dale | 606/87 |
| 4,907,577 | 3/1990 | Wu | 606/80 |
| 4,969,895 | 11/1990 | McLeod | 606/96 |
| 5,021,055 | 6/1991 | Burkinshaw | 606/87 |
| 5,035,699 | 7/1991 | Coates | 606/86 |
| 5,047,032 | 9/1991 | Jellicoe | 606/83 |

Primary Examiner—Robert A. Hafer
Assistant Examiner—Michael Brorr
Attorney, Agent, or Firm—Todd A. Dawson

[57] ABSTRACT

The milling guide of this invention provides a guide having a base with a track formed therein to slidably accommodate a milling device and guide the milling device along the bone. The milling device provides a smooth bone surface and the guide is provided to maintain the milling device generally transverse to the longitudinal axis of the tibia. A slider is carried by the track and accommodates the milling device to maintain the milling device generally perpendicular relative to the guide. The slider is shiftable within the guide in an medial-lateral plane. The milling device is shiftable relative to the slider and guide in the anterior-poster plane as well.

7 Claims, 3 Drawing Sheets

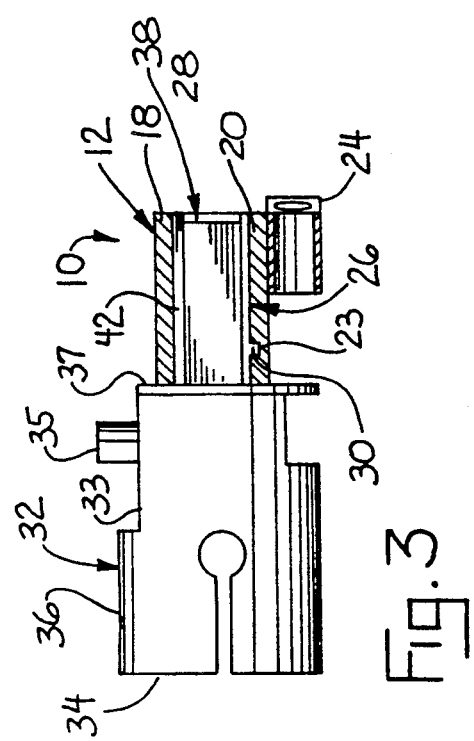
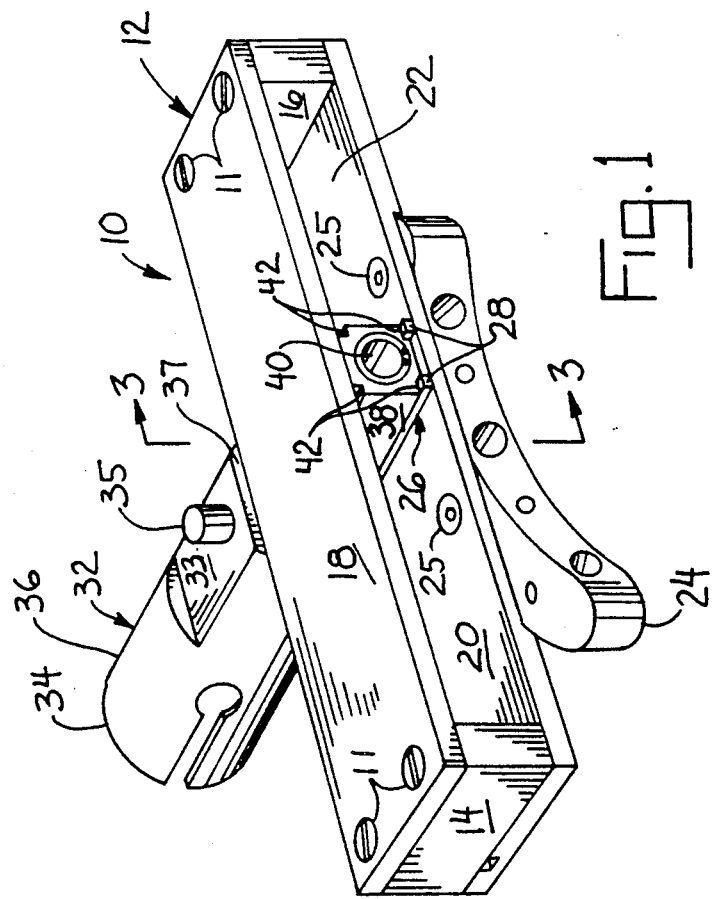

5,207,680

FRONT MILLING GUIDE FOR USE IN ORTHOPAEDIC SURGERY

FIELD OF THE INVENTION

This invention relates to a bone milling guide for use in orthopaedic surgery.

SUMMARY OF THE INVENTION

The device of this invention provides a guide having a base with a track formed therein to slidably accommodate a milling device and guide the milling device along the bone. The milling device provides a smooth bone surface and the guide is provided to maintain the milling device generally transverse to the longitudinal axis of the tibia. A slider may be carried by the track to accommodate the milling device and to maintain the milling device generally perpendicular relative to the guide. The slider is shiftable within the guide in a medial-lateral plane. The milling device is shiftable relative to the slider and guide in the anterior-poster plane as well. Optionally, the slider may be removed to give the surgeon greater freedom in lateral movement within the guide.

Accordingly, it is an object of the invention to provide for a novel milling guide.

Another object of the invention is to provide for a milling guide for connection to the front of a patient's tibia.

Still another object of the invention is to provide for a milling guide having a track and adapter for slidably accommodating a milling device in an anterior-posterior plane and a medial-lateral plane.

Yet other objects of the invention will become apparent upon a reading of the following description taken with the accompanying drawings.

BRIEF DESCRIPTION OF THE DRAWINGS

FIG. 1 is a perspective view of the milling guide of the invention.

FIG. 3 is a sectional view taken along line 3—3 of FIG. 1.

DESCRIPTION OF THE PREFERRED EMBODIMENTS

The preferred embodiments herein described are not intended to be exhaustive or to limit the invention to the precise forms disclosed. Rather, they are chosen and described to best explain the invention so that others skilled in the art might utilize their teachings.

Figure 2:
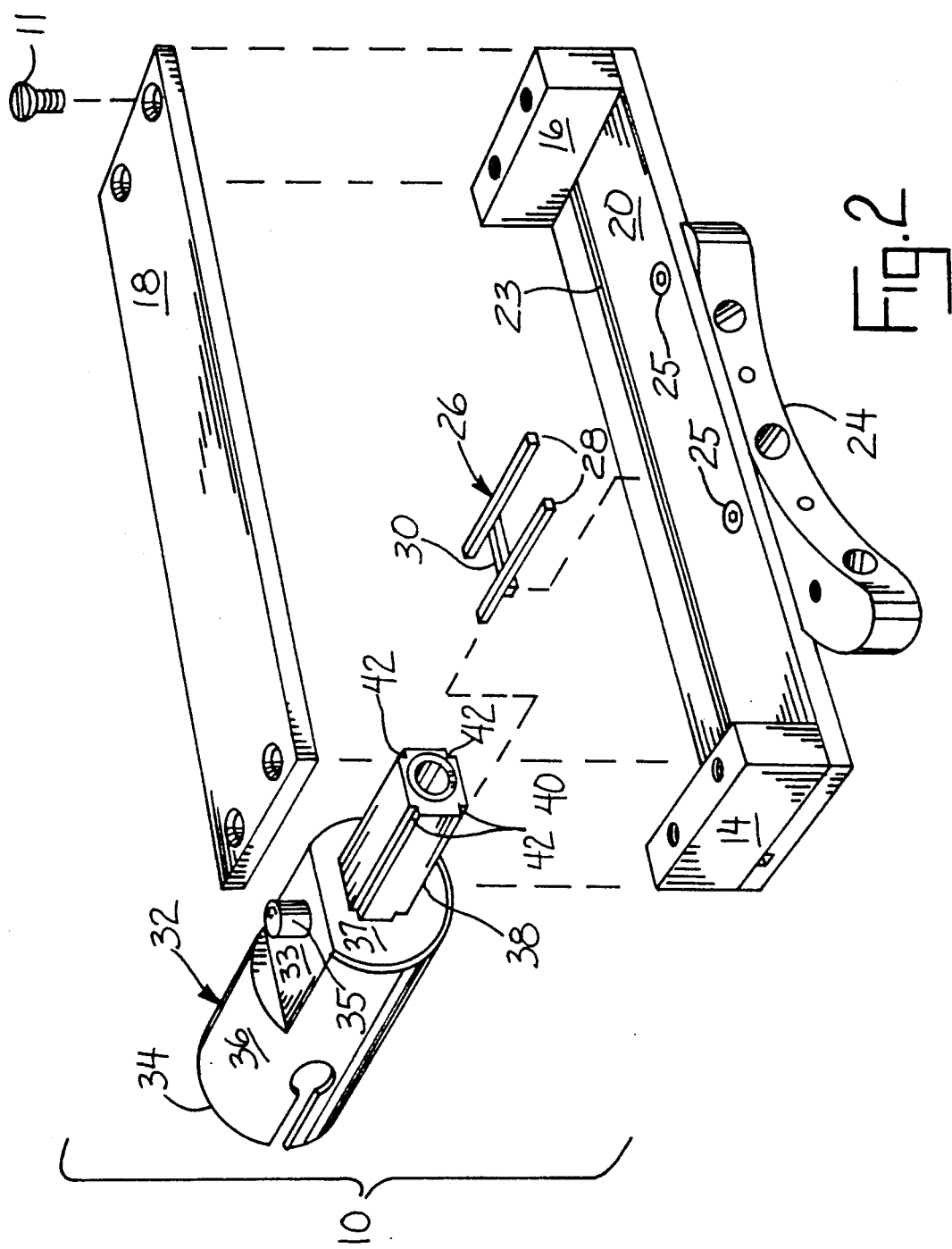
FIG. 2 is an exploded view of the milling guide of FIG. 1.

Referring now to FIGS. 1-3, milling guide 10 includes a base 12 having end walls 14, 16, a top wall 18 and a bottom wall 20 held together by screws 11. Walls 14, 16, 18 and 20 form a generally rectangular frame defining a rectangular interior opening 22. A groove or track 23 is provided in bottom wall 20 in communication with interior opening 22. A bracket 24 is connected to bottom wall 20 by screws 25 and extends downwardly therefrom. Bracket 24 is generally arcuate and includes a plurality of throughbores to accommodate screws or pins for connecting milling guide 10 to the proximal portion of the patient's tibia (not shown). A general H-shaped slide 26 is provided and includes a pair of spaced parallel legs 28 and an interconnecting brace 30. Brace 30 lies in a plane beneath legs 28 as shown and is shaped to be slidably received within track 23 of bottom wall 20. In the preferred embodiment, brace 30 and legs 28 are generally square in cross section and brace 30 is closely dimensioned to fit within groove 24 without significant anterior-posterior shifting. Brace 30 is slidable along the bottom wall within track 24 such that legs 28 ride on the upper surface of the bottom wall 20.

An adapter 32 is included for connection at one end 34 to a rotary power source such as a drill (not shown) and accommodates the shaft of a milling cutter (not shown) as explained below. Adapter 32 includes a generally cylindrical body 36 for clamping engagement about the housing of a drill (not shown). A protrusion 35 extends transversely relative to body 36 from a flattened area 33. An elongated nose portion 38 extends longitudinally from body 36 and is generally square in cross-section. A shoulder 37 is formed at the junction of body 36 and nose portion 38. A central bore 40 is formed through the longitudinal axis of nose portion 38 in communication with body 36 to freely accept the shaft of a milling cutter (not shown). A notch 42 is formed in nose portion 38 at each corner as illustrated in the figures. Notches 42 are formed to shiftably accommodate the spaced legs 28 of H-shaped slide 26. The nose portion of the adapter is positionable between the top wall 18 and bottom wall 20 of the guide between legs 28 of the H-shaped slide 26 as best illustrated in FIG. 1. So positioned, the top wall and bottom wall of nose portion 38 contact top wall 18 and bottom wall 20 of base 12.

In use, adapter 32 is connected to a rotary power source, such as a drill (not shown), and a milling cutter (also not shown) is inserted into the central bore 40 of the adapter and clamped within the chuck of the drill. A portion of the shaft of the milling cutter is journaled within the central bore of the adapter 32. After the knee joint is surgically exposed, milling guide 10 is secured to the proximal portion of the patient's tibia by pins or screws traversing the throughbores in bracket 24 and seating within the tibia. Slide 26, as mentioned previously, is carried by bottom wall 20 and is slidable along the bottom wall a guided by track 24. The surgeon shifts the slide 26 into contact with one of the end walls 14, 16 and positions the mill cutter (connected to the milling device) between the top wall 18 and bottom wall 20. The surgeon pushes the mill cutter through the guide until the adapter 32 is slidably positioned between the top and bottom wall of the guide. The parallel legs 38 of slide 26 are accommodated by two of the notches 42 of adapter 32. The engagement of notches 42 and legs 38 maintain the adapter and connected mill cutter perpendicular to the base 12.

With the mill cutter, adapter and guide positioned as described above, the surgeon activates the rotary power source or drill to rotate the mill cutter. As the cutter rotates, the surgeon slides the cutter across the bone to remove the upper surface of the bone. It should be understood that the mill cutter should be long enough to reach the posterior edge of the bone. It may be necessary to pass over the bone surface a second time to obtain the desired flat surface. Further, it may be desirable to initially mill the bone surface with a more aggressive cutter to remove a majority of the bone material. After the "rough" milling has been completed, the surface could be remilled with a less aggressive mill to produce the desired smooth surface.

Figure 4:
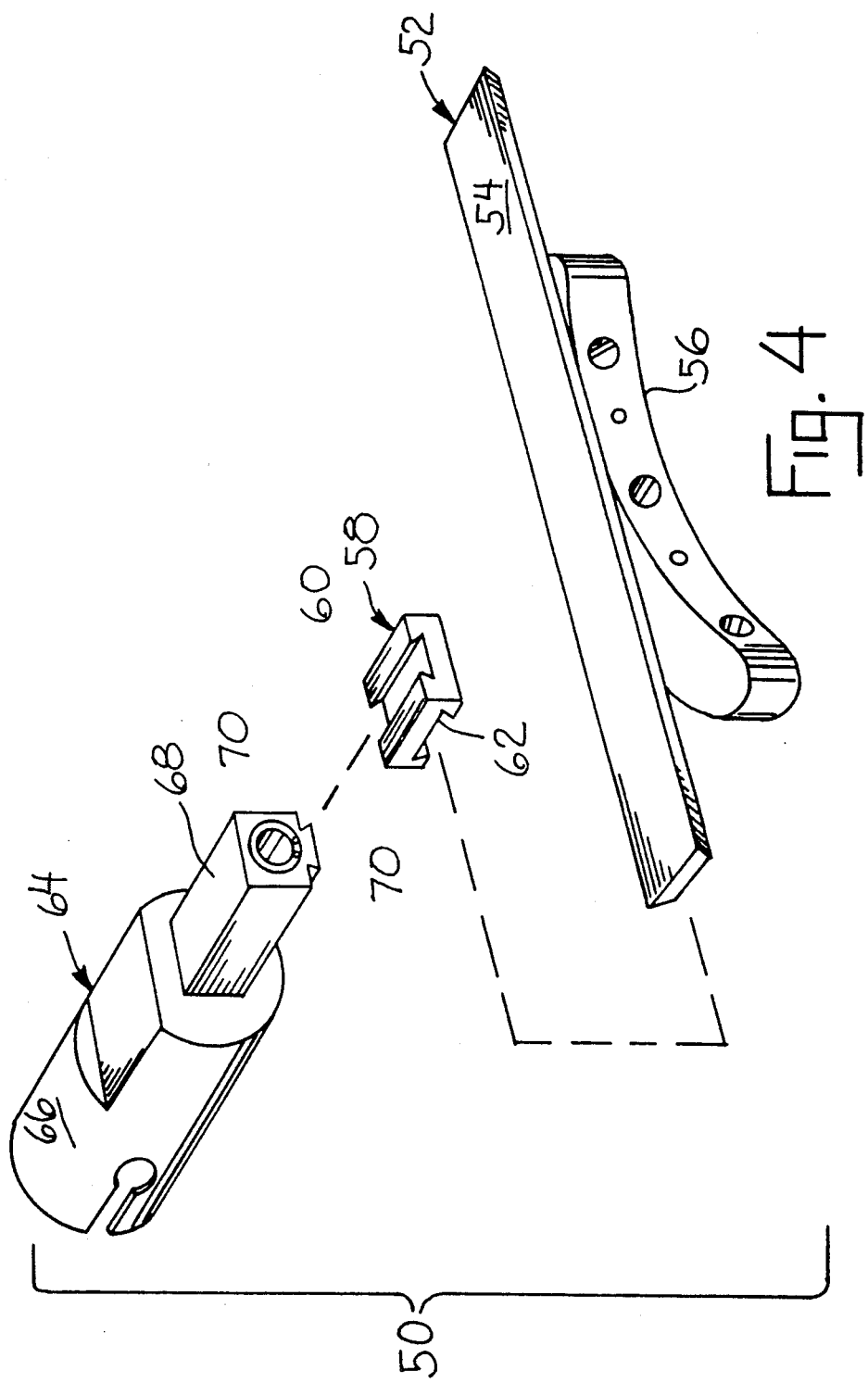
FIG. 4 is an exploded view of a second embodiment of the invention with portions omitted for clarity.

Referring now to FIG. 4, an alternative embodiment of the invention is illustrated. Guide 50 of FIG. 4 includes a base 52 having a bottom wall 54, spaced side walls (not shown) and a top wall (also not shown). The side walls and top walls of the base are not shown for to better illustrate the novelty of guide 50; however, in practice, the side walls and top wall closely resemble the base of FIGS. 1-3. As illustrated, bottom wall 54 is generally trapezoidal in cross section. An arcuate bracket 56 is connected to bottom wall 54 by a plurality of screws (not shown). A slide 58 is provided and includes a pair of dovetail grooves 60, 62 transverse to one another and formed in opposite faces of the slide 58 as shown in FIG. 6. Adapter 64 includes a generally cylindrical housing 66 for accommodating a rotary drill (not shown). A nose portion 68 extends longitudinally therefrom and includes a longitudinal bore 70 for accommodating the shaft of a milling cutter (not shown). The periphery of nose portion 68 is generally square. A rib 70 extends longitudinally along one side wall of the nose portion and is generally of a dovetailed cross section.

In use, the bracket 50 of FIG. 4 is connected to the exposed portion of a bone to be milled. Slide 58 is carried by bottom wall 54 such that the dovetail groove 62 accommodates the dovetail bottom wall in a sliding connection. The dovetailed rib of nose portion 68 is slid within the dovetail groove 60 of slide 58. In this orientation, the adapter (with milling cutter and rotary drill attached) is slidable in one direction along the bottom wall and in a second position perpendicular to the bottom wall.

It should be understood that the invention should not be limited to the precise details of the above embodiments, but may be modified in keeping with the appended claims.

We claim:

1. A milling guide for connection to an exposed portion of a bone to guide a milling device longitudinally across an upper surface f the bone, said milling guide comprising, a base having attachment means for connecting the guide to the bone, said base being adapted to extend laterally adjacent the bone, said base including a track means extending longitudinally along the base member, a slide means carried by the base in sliding engagement with said track means for accommodating a portion of a milling device, wherein with a milling device connected to said guide the milling device is slidable relative to said base in a predetermined pattern within the track means, said slide means being positionable with the track means and being substantially smaller than said track means such that said milling device is movable laterally across the exposed bone form one end of the track means toward an other end of the track means.

2. The guide of claim 1 further including an adapter having a elongated nose portion, said adapter for connection to said milling device and includes a longitudinal bore formed therethrough for rotatably accommodating a portion of a milling cutter.

3. The guide of claim 2 wherein said base member includes a pair of space side walls, a top wall and a bottom wall connected so as to form a generally rectangular frame defining a rectangular frame having a generally rectangular opening, said nose portion being slidably accommodated within the opening of said base in frictional engagement with the top wall and bottom wall of said base, said nose portion being slidable between said spaced side walls.

4. The guide of claim 3 wherein said track means includes a groove formed in said bottom wall of said base member, said slide including a portion slidably accommodated within said groove, said slide further including a leg portion slidably contacting said bottom wall and generally perpendicular to said groove, said nose portion including a notch for accommodation of said leg such that as said slide and said nose portion slides along said bottom wall as guided by said groove said nose portion is held such that said longitudinal bore of said adapter is generally perpendicular to said base.

5. The guide of claim 3 wherein said track means includes a rib extending integrally above said bottom wall of said base member, said slide including a lower notch for slidably accommodating said rib, said slide further including an upper notch perpendicular to said lower notch, said nose portion including a rib for sliding accommodation within said upper groove of said slide, such that as said slide and said nose portion shift along said bottom wall as guided by said rib of said bottom wall said nose portion is held such that said longitudinal bore of said adapter is generally perpendicular to said base.

6. The guide of claim 4 wherein the engagement between said nose portion and said slide and the engagement between said slide and said bottom wall constitutes means for permitting said nose portion to shift in a first direction along said bottom wall and in a second direction generally perpendicular to said bottom wall.

7. A milling guide for connection to an exposed portion of a bone to guide a milling device along an upper surface of the bone, said milling guide comprising, a base having attachment means for connecting the guide to the bone, said base being adapted to extend laterally across the bone, said base including a track means extending longitudinally along the base member, a slide means carried by the base in sliding engagement with said track means for accommodating a portion of a milling device, wherein with a milling device connected to said guide them milling device is slidable relative to said base in a predetermined pattern, the device further including an adapter having an elongated nose portion, said adapter for connection to said milling device and includes a longitudinal bore formed therethrough for rotatably accommodating a portion of a milling cutter, said base member including a pair of space side walls, a top wall and a bottom wall connected so as to form a generally rectangular frame defining a rectangular frame having a generally rectangular opening, said nose portion being slidably accommodated within the opening of said base in frictional engagement with the top wall and bottom wall of said base, said nose portion being slidable between said spaced side walls, said track means includes a groove formed in said bottom wall of said base member, said slide including a portion slidably accommodated within said groove, said slide further including a leg portion slidably contacting said bottom wall and generally perpendicular to said groove, said nose portion including a notch for accommodation of said leg such that as said slide and said nose portion slides along said bottom wall as guided by said groove said nose portion is held such that said longitudinal bore of said adapter is generally perpendicular to said base.

* * * * *